Figure 1:
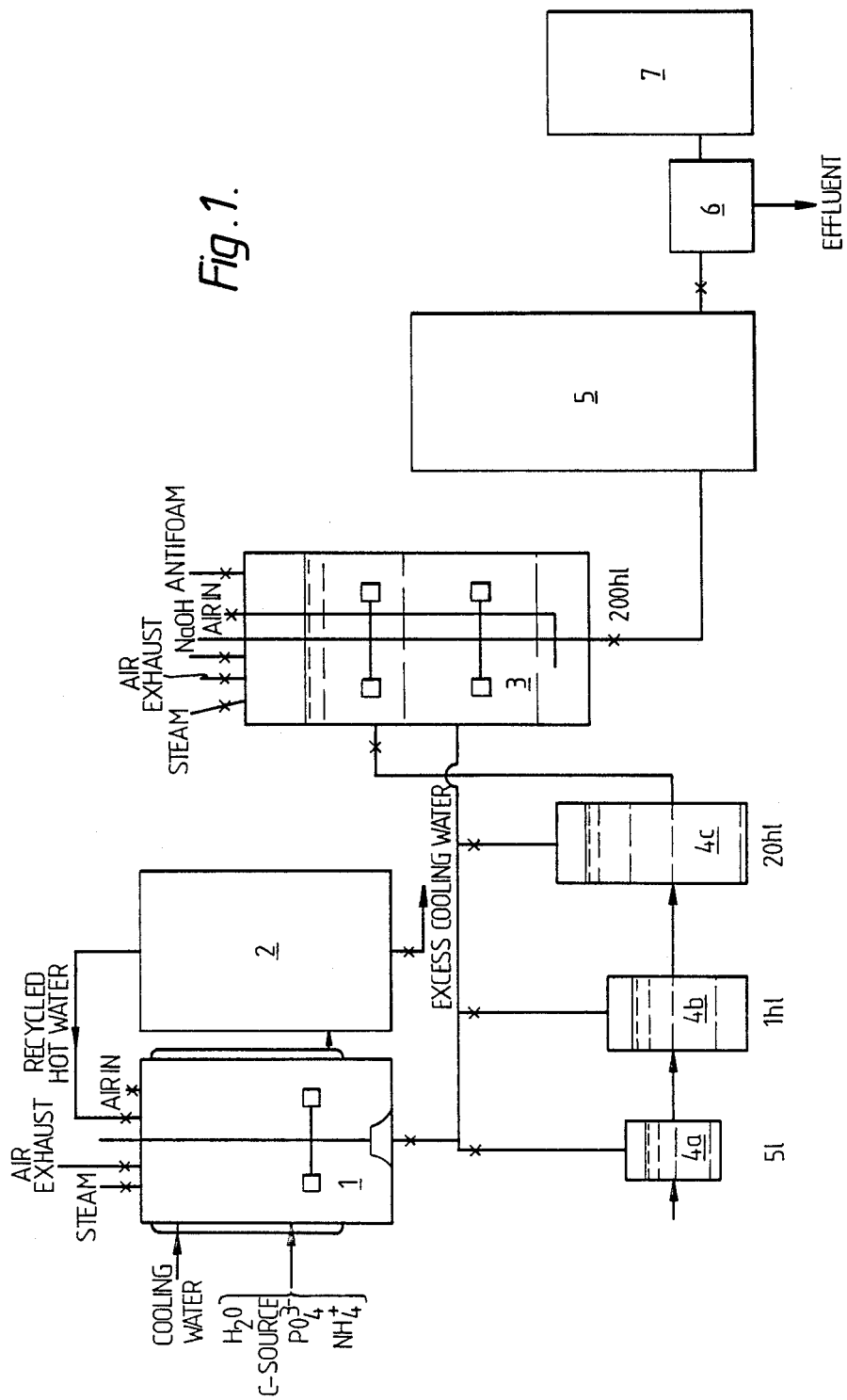

United States Patent [19]

Herbert et al.

[11] Patent Number: 4,851,343

[45] Date of Patent: Jul. 25, 1989

[54] MICROBIOLOGICAL PRODUCTION OF ESSENTIAL FATTY ACIDS

[75] Inventors: Rodney A. Herbert; Stephen M. Keith, both of Angus, Scotland

[73] Assignee: Efamol Limited, Surrey, England

[21] Appl. No.: 702,947

[22] Filed: Feb. 19, 1985

[30] Foreign Application Priority Data

Feb. 21, 1984 [GB] United Kingdom ............... 8404463

[51] Int. Cl.$^4$ .............................................. C12P 7/64
[52] U.S. Cl. .................................. 435/134; 435/939; 260/413
[58] Field of Search ................. 435/134, 939; 260/413

[56] References Cited

PUBLICATIONS

The Merck Index, 10th Edition, 1983, p. 790.

Gellerman et al, Biochim. et Biphys. Acta, vol. 573, (1975), pp. 23–30.

Ratledge, Progress in Industrial Microbiology, vol. 16, (1980), pp. 119–206.

Primary Examiner—Charles F. Warren
Assistant Examiner—Carolyn S. Greason
Attorney, Agent, or Firm—Nixon & Vanderhye

[57] ABSTRACT

Production of γ-linolenic acid, by growth of a diffused mycelial inoculum of Rhizopus arrhizus in a stirred, aerated nutrient medium containing a carbohydrate energy source and an inorganic nitrogen source at a carbon:nitrogen ratio of 20:1 to 60:1 maintained at a temperature of 25° C.±2° C. and a pH of 3.75 to 6.25 in the presence of a foam breaker, until a γ-linolenic concentration of at least 1.0 g/liter of medium is reached, harvesting the organism, and extraction of lipid containing the γ-linolenic acid.

4 Claims, 2 Drawing Sheets

MICROBIOLOGICAL PRODUCTION OF ESSENTIAL FATTY ACIDS

This invention relates to the microbiological production of essential fatty acids.

GENERAL

During a current screening programme thirty-five strains of yeasts and fungi have been examined for γ-linolenic acid production. Data in Tables 1 and 2 show that neither yeasts nor higher fungi produce γ-linolenic acid. The C18:3 fatty acid produced by these fungi is α-linolenic acid and, with the exception of *Aureobasidium pullulans,* the quantities formed are small. Members of the lower fungi, belonging to the order Mucorales, however are promising γ-linolenic acid producers (see Table 3) and with the exception of *Mucor hiemalis* and *Mortierella vinaceae* this is the sole isomer produced. Here lower fungi were grown in batch culture (2 liters) on a simple mineral salts medium comprising (g/l of distilled water), glucose 40 g, asparagine 2.0 g, $KH_2PO_4$ 0.5 g, $MgSO_4.7H_2O$ 0.25 g, thiamine hydrochloride 0.005 g, at pH 7.0 and 25° C. for 5-7 days before harvesting. The culture had by this time achieved the stationary phase of growth and lipid accumulation was occurring. From the data in Table 3 a number of potential γ-linolenic acid producers can be selected on the basis of total lipid synthesised and the proportion which is the C18:3 n-6 isomer. On the basis of % γ-linolenic acid produced, expressed as a % of dry weight *Phycomyces blakesleeanus* was the highest producer, however the organism grew preferentially in shake culture as a mycelial mat and appeared particularly sensitive to stirring or shaking on an orbital shaker. Members of the genera Cunninghamella (*C. echinulata* and *C. elegans*), Mucor (*M. plumbeus*) and Rhizopus (*R. stolonifer, R. arrhizus* and *R. oryzae*) produced significant quantities of γ-linolenic acid and proved much more amenable to growth in shake flask culture.

ORGANISMS FOR γ-LINOLENIC ACID

Two isolates *R. arrhizus* and *C. elegans* were selected for further work since they grew rapidly, produced spores readily which made media inoculation simple and appeared resistant to shear stress when grown in a batch fermenter. Data in Table 4 show the total lipid yield of *R. arrhizus* when grown in a batch stirred culture on the mineral medium described previously. The carbon:nitrogen ratio of the media was either 40:1 or 200:1 and automatic pH dosing of the culture was also included since in the absence of pH control the pH of the growth medium fell to pH 3 during exponential growth. The data (Table 4) show that a C:N ratio of 40:1 with pH control (pH 7.0 maintained) *R. arrhizus* produced 17.5% of its dry weight as γ-linolenic acid. The omission of pH control and/or the use of 200:1 C:N ratio led to a marked decline in γ-linolenic acid production in the organism. The use of a spore inoculum in this small scale work rather than a mycelial inoculum ensured that growth occurred throughout the fermentation medium rather than at discrete centres.

In subsequent fermentation runs in a 3 liter batch fermenter, with a higher stirring speed, *R. arrhizus* grew in a filamentous form and was able to withstand the high shear forces involved without loss of viability. A noticeable feature when growing *R. arrhizus* under these conditions was a tendency of the culture to foam and this was controlled by the addition of non-ionic anti-foam reagent (Antifoam C).

Comparative studies growing *C. elegans* in a similar batch culture fermenter showed it to be less valuable for γ-linolenic acid production than *R. arrhizus.* In the original screening programme (Table 3) *C. elegans* accumulated considerable quantities of lipid (32.7% lipid) and γ-linolenic acid (19.4%), but the organism produces spores less easily than *R. arrhizus* and thus (again in this small scale work) the number of growing points in the fermenter are fewer and the mycelium tends to clump. However despite these difficulties the data in Table 5 show that *C. elegans* produces considerable quantities of lipid and whilst the γ-linolenic acid content is lower, the % expressed in terms of dry weight is still significant (4.2%). In these experiments the culture of *C. elegans was grown at a C:N ratio of* 40:1 and the nature of the N-source on lipid accumulation and γ-linolenic acid content assessed. Ammonia grown cultures produced a lower total lipid content than asparagine cultures but this was compensated for by an increased γ-linolenic acid content of the ammonia grown cultures.

THE INVENTION

Overall, *R. arrhizus* has considerably greater value for industrial capacity for the production of γ-linolenic acid, and the invention accordingly lies in the use of this organism and particularly its strain IMI 57412 and corresponding strain USPA 702947 deposited as accession number CMI CC No. 320102 at the Commonwealth Mycological Institute, Kew, United Kingdom in a stirred, aerated nutrient medium containing a carbohydrate energy source and an inorganic nitrogen source giving a carbon:nitrogen ratio of 20:1 to 60:1, inoculated with a diffuse mycelial culture of the organism, and maintained at a temperature of 25° C.±2° C. and a pH of 3.75 to 6.25, preferably 6±0.2, in the presence of a foam breaker. Desirably, low-speed stirring allowing filamentous growth is used, e.g. up to 200 rpm with a typical stirrer, and aeration rate at 0.2 to 0.5 volumes air/min/unit volume of medium.

Under these closely controlled conditions optimum yields of γ-linolenic acid are obtained. Suitable carbohydrate energy sources include glucose, preferably in the form of such inexpensive materials as hydrolysed starch, e.g. maize starch. In the following medium, for example:

| COMPONENT | CONCENTRATION g/l |
| --- | --- |
| Glucose | 151.2 |
| $NH_4Cl$ | 5.6 |
| $MgSO_4.7H_2O$ | 1.2 |
| $KH_2PO_4$ | 6.0 |
| Yeast Extract | 0.12 | a yield of approximately 15 g dry weight/liter fermentation medium is obtainable with a lipid yield of circa. 45% dry weight and a γ-linolenic acid content on total lipids of 15 to 20%, i.e. 1.0 to 1.35 g/liter fermentation medium. The medium is maintained with a carbon-nitrogen ratio such that growth is nitrogen limited, for optimum γ-linolenic acid yield.

TABLES OF DATA

TABLE 1

LIPID PRODUCTION AND FATTY ACID COMPOSITION OF YEASTS AND FUNGI

| Organism | Lipid Yield % | 16:0 | 16:1 | 18:0 | 18:1 | 18:2 | 18:3 |
|---|---|---|---|---|---|---|---|
| Hansenula subpellicosa (exponential culture) | 2.9 | 16.3 | 6.41 | 3.16 | 36.36 | 34.9 | 1.2 |
| Hansenula subpellicosa (stationary phase) | 19.8 | 17.1 | 3.25 | 4.78 | 29.8 | 38.3 | 6.6 |
| Rhodotorula rubra (exponential phase) | 4.3 | 16.6 | 4.6 | 4.2 | 40.66 | 29.27 | 1.9 |
| Rhodotorula rubra (stationary phase) | 17.4 | 16.1 | 1.75 | 2.4 | 47.99 | 26.0 | 3.9 |
| Candida utilis G1 | 16.7 | 13.5 | 1.0 | 7.2 | 46.9 | 28.1 | 0.5 |
| Debaryomyces ansenula | 5.0 | 26.8 | 5.3 | 2.4 | 41.4 | 10.9 | 2.2 |
| Rhodotorula glutinis | 15.6 | 10.4 | 1.5 | 3.7 | 80.2 | 1.0 | 0.8 |
| Aureobasidium pullulans | 14.9 | 15.0 | 0.8 | 2.9 | 13.2 | 54.9 | 12.3 |
| Aureobasidium pullulans (mycelium) | 26.4 | 15.4 | 1.1 | 4.12 | 20.1 | 45.7 | 13.2 |
| Aureobasidium pullulans (spores) | 56.0 | 13.12 | 1.0 | 4.9 | 45.1 | 33.0 | 0.9 |
| Rhodotorula rubra | 24.8 | 11.9 | 1.9 | 3.42 | 77.9 | 2.03 | 0.7 |
| Candida vini | 11.5 | 20.25 | 1.19 | 9.9 | 30.52 | 28.8 | 2.1 |

TABLE 2

LIPID YIELD AND FATTY ACID COMPOSITION OF FILAMENTOUS FUNGI

| Organisms | Lipid Yield % | 16:0 | 16:1 | 18:0 | 18:1 | 18:2 | 18:3 |
|---|---|---|---|---|---|---|---|
| Aspregillus nidulans | 32.5 | 11.6 | 8.3 | 2.5 | 16.0 | 37.9 | 1.1 |
| Aspergillus niger | 11.9 | 10.7 | 9.7 | 1.7 | 14.9 | 39.1 | 1.9 |
| Aspergillus terreus | 8.9 | 23.0 | 1.2 | 1.6 | 14.1 | 40.0 | 1.4 |
| Fusarium oxysporum | 16.3 | 21.0 | 0 | 4.3 | 39.3 | 25.6 | 0.7 |

NOTES (Tables 1 and 2)
(i) 18:3 isomer is α-linolenic acid. No γ-linolenic acid present. Traces only of C20 acids.
(ii) Organisms used were from various sources including wild types.
(iii) Lipid yields on total dry weight, % fatty acids by weight.

TABLE 3

LIPID YIELD AND γ-LINOLENIC ACID PRODUCTION BY LOWER FUNGI GROWN IN SHAKE FLASK CULTURE ON A DEFINED MINERAL MEDIUM

| Organism | Strain (IMI number) | Lipid Yield % | 18:3n-6 | 18:3n-3 | 18:3/dry wt |
|---|---|---|---|---|---|
| Mucor mucedo | 26441 | 23.3 | 12.2 | 0 | 2.8 |
| Mucor hiemalis | 103746 | 28.9 | 6.7 | 0.6 | 1.9 |
| Mucor circinelloides | 55452 | 14.3 | 12.9 | 0 | 1.8 |
| Mortierella vinaceae | 147433 | 30.0 | 6.4 | 1.3 | 1.9 |
| Rhizopus arrhizus | 57412 | 19.6 | 14.7 | 0 | 2.9 |
| Mortierella ramanniana | 144619 | 18.1 | 8.2 | 0 | 1.5 |
| Conidiobolus coronatus | 145949 | 52.2 | 2.1 | 0 | 1.1 |
| Rhizopus stolonifer | 17314 | 41.4 | 14.5 | 0 | 6.0 |
| Mucor plumbeys | 14781 | 30.3 | 17.1 | 0 | 5.2 |
| Cunninghamella echinulata | 45772 | 28.4 | 15.4 | 0 | 5.4 |
| Cunninghamella elegans | 21199 | 32.2 | 13.0 | 0 | 5.7 |
| Rhizopus oryzae | 21602 | 32.7 | 13.0 | 0 | 5.7 |
| Phycomyces blakesleeanus | 63129 | 49.1 | 17.5 | 0 | 8.5 |
| Mucor miehei | 125824 | 39.2 | 4.0 | 0 | 1.5 |

NOTES (Table 3)
(i) With the exception of Mortierella vinaceae and Mucor hiemalis no α-linolenic acid was produced.
(ii) All strains are from the Mycological Institute, Kew.
(iii) No C20 acids detected.

TABLE 4

LIPID AND γ-LINOLENIC ACID PRODUCTION BY RHIZOPUS ARRHIZUS IMI 57412 IN A 2 LITER STIRRED BATCH FERMENTER WITH AND WITHOUT pH CONTROL

| C:N | pH control | Lipid Yield % | 18:3n-6 | 18:3/dry wt |
|---|---|---|---|---|
| 40:1 | + | 74.3 | 23.5 | 17.5 |
| 40:1 | − | 75.6 | 16.2 | 12.2 |
| 200:1 | + | 75.5 | 15.7 | 11.9 |
| 200:1 | − | 55.7 | 17.2 | 9.6 |

TABLE 5

LIPID YIELD AND γ-LINOLENIC ACID PRODUCTION BY CUNNINGHAMELLA ELEGANS IMI 21199 IN A 2 LITER BATCH FERMENTER

| N-source | Lipid Yield % | 18:3n-6 | 18:3/dry wt |
|---|---|---|---|
| NH4+ | 56.6 | 7.43 | 4.2 |
| Asparagine | 64.6 | 6.58 | 4.2 |

NOTES (Tables 4 and 5)
(i) No α-linolenic acid was detected in any sample.
(ii) % basis as before.

PROCESS DETAILS

Based on the diffuse mycelial inoculum that we have found necessary for good growth throughout the medium the overall production of γ-linolenic acid on a commercial basis by Rhizopus arrhizus IMI 57412 is shown schematically in FIG. 1. The fermentation medium as given earlier comprises a simple mineral salts-sugar solution which is prepared and sterilised in the medium cooker 1.

The actual glucose source is brewing-grade hydrolysed maize starch (99% glucose). After sterilisation the fermentation medium is then cooled to 25° to 30° C. by means of a cooling coil and jacket and the recovered hot water stored in a lagged holding tank 2. The bulk of the cooled fermentation medium is transferred to a previously steam sterilised main production fermenter 3 whilst a residual volume of medium (2,200 liters) is retained for filling the seed vessel fermenters 4a, 4b, 4c. The culture inoculum is grown up in these in increasing volumes (5 l, 100 l, 20 hl) the final one of which is used to inoculate the main production fermenters. An inoculum ratio of 1:10 enables a rapid initiation of growth in the main production fermenter and a growth cycle of 3.5 days optimum for lipid and γ-linolenic acid yield. During the growth cycle in the production fermenters the culture is continuously stirred (50–100 rpm) and sparged with sterile air (circa. 5,000 liters/minute). During the exponential growth phase of the culture considerable heat is generated and the fermenter needs cooling to maintain a growth temperature of 25° C. This is effected by the use of refrigeration units. At the completion of the growth cycle the spent medium plus fungal mycelium is run off into a holding tank 5 prior to cell separation by continuous centrifugation. The cell harvesting process is an automatic operation using continuous centrifuges 6 with solids ejection facilities. The separated de-watered mycelium is held in a refrigerated holding tank 7 at 10% water content until required for oil extraction. Upon completion of each stage of the cycle the empty vessels (production fermenter, cooker, seed vessels) are cleaned in place, re-sterilised with steam where necessary and the process described above repeated.

Figure 2:
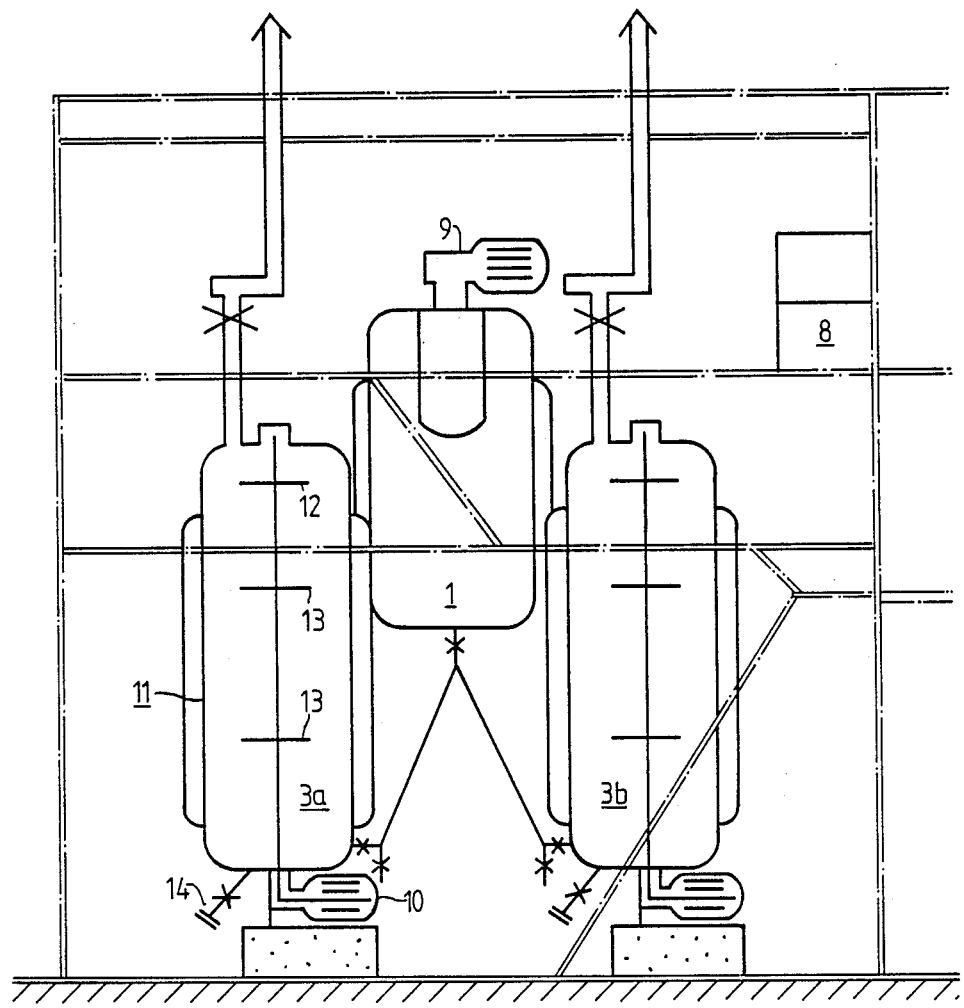

The lay-out of the plant, shown in FIG. 2, takes advantage of gravity transfer wherever possible and makes optimal use of available space.

A suitable lay-out is four production fermenter vessels and ancillary equipment. The medium cooker 1 is mounted centrally in an elevated position between the four fermenter vessels two of which 3a, 3b are seen so that transfer of the prepared sterile medium from the cooker can be effected by a combination of gravity and differential air pressure. In a similar manner the final stage seed fermenter vessels (20 hl) (such as 4c, FIG. 1, not seen) are mounted above the production fermenters so that transfer of the inoculum can be effected by gravity and air pressure. Exhausts from the production fermenters, after passing through filters, vent through the roof.

The cooker 1 can be designed as a central facility to provide sterile fermentation media not only for a number of production fermenters 3 but also for the seed fermenters on a daily basis. It consists of a jacketed, top-drive stirred (motor 9) tank of 220 hl capacity which can be cleaned in place and steam sterilised. To avoid problems of precipitation and caramelisation arising from the incompatability of phosphates and sugars during media sterilisation the preparation and sterilisation of the inorganic media components is carried out separately in an auxiliary cooker (capacity 10 hl) and mixed aseptically with the remainder of the medium after cooling to a suitable temperature.

Each main production fermenter vessel is constructed as a jacketed vessel the inner skin of which is fabricated from food grade stainless steel. It is stirred by a bottom drive motor assembly 10 operating stirrers 13 through a reduction gearbox. Cleaning of the internal surfaces is by a permanently installed "clean in place" system (tank 8) and steam sterilisation of the vessel. Temperature control of the fermentation process (25° C.) is achieved by continuous sensing of the culture medium which in turn controls the flow of chlorinated water circulating through the fermenter jacket 11 and internal cooling coils (not shown). The pH of the medium is continuously monitored throughout the growth cycle and maintained by automatic addition of alkali when required. Foam suppression is achieved by a mechanical foam breaker 12 in conjunction with, if necessary, timed anti-foam (i.e. chemical foam breaker) additions. The anti-foam used should be chosen to avoid clumping of the mycelium rather than the desired diffuse filamentous growth and silicone anti-foams with non-ionic emulsifiers are suitable, for example that sold by Midland Silicones U.K. as research grade anti-foam. Upon completion of the growth cycle the spent medium plus the mycelium is discharged at 14 into a refrigerated holding tank (as 5, FIG. 1, not seen) to enable the fermenter to be re-cleaned, re-sterilised, refilled and re-inoculated.

Following the discharge of the spent medium and mycelium into the holding tank 5 the separation of the cells is achieved using standard continuous centrifugation methods. The ejected solids are stored until required for oil extraction whilst the spent medium is discharged.

We claim:

1. A process for producing gamma-linolenic acid by (1) growing a diffused mycelial inoculum of *Rhizopus arrhizus* in a stirred, aerated nutrient medium containing a carbohydrate energy source and an inorganic nitrogen source at a carbon:nitrogen ratio of 20:1 to 60:1, maintained at a temperature of 25° C.±2° C. and a pH of 3.75 to 6.25 in the presence of a foam breaker, until a gamma-linolenic concentration of at least 1.0 g/liter of medium is reached, (2) harvesting the organism, and (3) extracting lipid containing the gamma-linolenic acid.

2. The process according to claim 1, wherein the organism is *Rhizopus arrhizus* IMI 57412 (Mycological Institute, Kew).

3. The process according to claim 1, wherein the pH is 6±0.2.

4. The process according to claim 1, wherein aeration is at 0.2 to 0.5 volumes air/minute/volume of medium.

* * * * *